US006973846B2

(12) United States Patent
Bremer et al.

(10) Patent No.: US 6,973,846 B2
(45) Date of Patent: Dec. 13, 2005

(54) SAMPLE HANDLING DEVICE FOR AN ANALYTICAL INSTRUMENT

(75) Inventors: Ralf Bremer, Oberhausen (DE); Bernhard Rose, Dusseldorf (DE)

(73) Assignee: Gerstel Systemtechnik GmbH & Co., Mulheim (DE)

( * ) Notice: Subject to any disclaimer, the term of this patent is extended or adjusted under 35 U.S.C. 154(b) by 203 days.

(21) Appl. No.: 10/429,224

(22) Filed: May 2, 2003

(65) Prior Publication Data

US 2003/0233893 A1      Dec. 25, 2003

(30) Foreign Application Priority Data

May 3, 2002   (DE)   ................ 102 19 790

(51) Int. Cl.[7] ............................................. G01N 35/10
(52) U.S. Cl. ................ 73/864.25; 73/864.31
(58) Field of Search ............. 73/863, 864.21, 73/864.22, 864.23, 864.24, 864.25, 864.31, 73/864.73, 864.74, 863.21, 23.41, 23.42, 73/61.59, 863.32; 422/100

(56) References Cited

U.S. PATENT DOCUMENTS 4,198,483 A * 4/1980 Sogi et al. ................ 435/309.1
5,525,298 A * 6/1996 Anami ........................ 422/63
5,756,905 A   5/1998 Ueda

* cited by examiner

*Primary Examiner*—Robert Raevis
(74) *Attorney, Agent, or Firm*—Patterson, Thuente, Skaar & Christensen, P.S.

(57) ABSTRACT

The invention relates to a sample handling device for an analytical device, comprising a sampler provided with a holder, a movable holding arm for the holder and a support for the holder, said support being arranged in a stationary manner with respect to the holding arm, said holder being transferable between a suspended position on the support and a position located on the holding arm and being releasable from the holding arm by a pulling force exerted by the holding arm substantially perpendicular to the longitudinal direction of the latter.

20 Claims, 9 Drawing Sheets

SAMPLE HANDLING DEVICE FOR AN ANALYTICAL INSTRUMENT

FIELD OF THE INVENTION

The invention relates to a sample handling device for an analytical instrument, in particular a chromatograph. Such a device is used to take, prepare and handle samples to be anally by a chemical analysis unit which may be provided with a separation device for sample components like a chromatograph, especially a gas chromatography.

BACKGROUND OF THE INVENTION

Sample preparation and injection devices, called autosamplers, are known for chromatographs, in particular gas chromatographs. These autosamplers comprise a holding arm which can be moved in three mutually perpendicular directions for a holder of a sampler. Autosamplers of this type are designed for a predetermined, simple sequence, for example sampling by means of a syringe from a vial and discharging the sample into a sample discharge system of an analytical instrument, and a type of samplers provided for this sequence, for example syringes of a specific size. They can neither be used flexibly nor used for other types of samplers without manual conversion. In order to permit a more complicated sequence, it is known to arrange two autosamplers one above the other, each of which is then used for a predetermined programme sequence. However, this is firstly complicated and secondly substantially more complex in terms of the programme sequence. Arrangements of this type are also restricted to two autosamplers and therefore also to two types of samplers, because of the necessary lifting heights.

SUMMARY OF THE INVENTION

It is therefore an object of the invention to provide a sample handling device which permits substantially more flexible automatic handling of different samplers.

A further object of the invention is to provide a sample handling device with little expenditure on equipment.

A still further object of the invention is to provide a sample handling device of a simplified construction.

The invention thus relates to a sample handling device for an analytical device, comprising a sampler provided with a holder, a movable holding arm for the holder and a support for the holder, said support being arranged in a stationary manner with respect to the holding arm, said holder being transferable between a suspended position on the support and a position located on the holding arm and being releasable from the holding arm by a pulling force exerted by the holding arm substantially perpendicular to the longitudinal direction of the latter.

Because a plurality of holders arranged to be stationary in relation to a holding arm are provided, it being possible for the latter for example to be moved in three mutually perpendicular directions, as a result of the fact that the holder in each case for a sampler can be transferred between a suspended position on one of the supports and a position located on the holding arm, it being possible for the respective holder to be released from the holding arm by a pulling force exerted by the holding arm substantially at right angles to the longitudinal direction of the latter, automatic handling of different samplers, which are each held by a holder, can be carried out. By means of suitable software, a programme sequence with regard to sample preparation, sampling, sample discharge, transferring samples or samplers between various stations and/or for preparing samplers can proceed automatically, including the holder change, in a task-specific manner by using different samplers, which can be exchanged with their associated holder.

The sample handling device can also serve as a robot for the automation of thermodesorption sequences, in which samples are picked up by a carrier and these are then introduced into a thermodesorption device, where the samples are thermodesorbed and subsequently analysed, for example by gas chromatography.

Further objects, embodiments and advantages of the invention can be gathered from the following description.

BRIEF DESCRIPTION OF THE DRAWINGS

The invention will be explained in more detail below with reference to exemplary embodiments illustrated in the appended drawings.

DETAILED DESCRIPTION OF PREFERRED EMBODIMENTS

Figure 1:
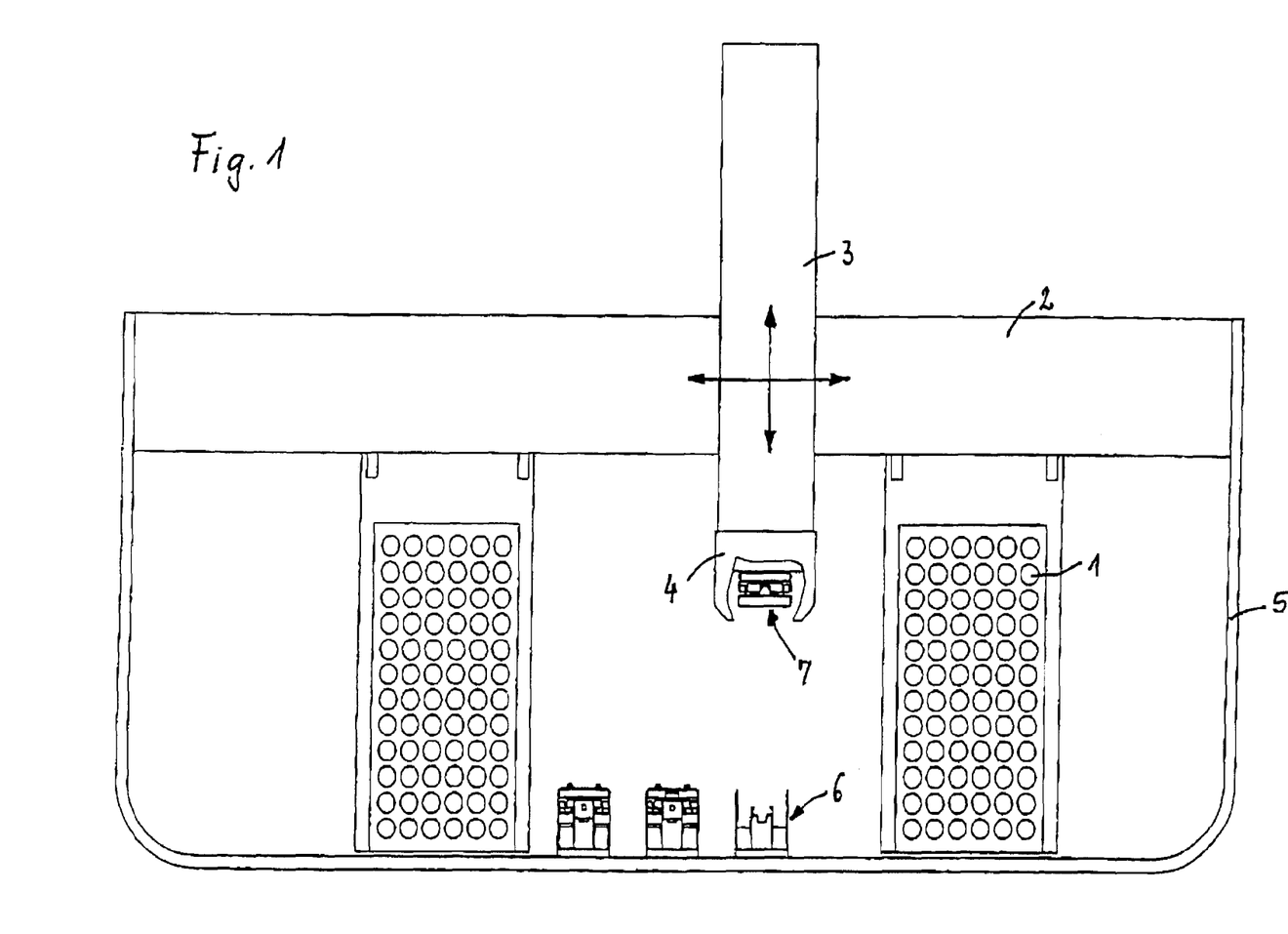
FIG. 1 shows, schematically in plan view, a sample handling device of the invention usuable for a gas chromatograph.

The sample handling device shown in FIG. 1 for a sample analytical instrument such as a gas chromatograph (or a liquid chromatograph, a mass spectrometer or the like) is used for handling samples to be analysed, that it to say for sample preparation, for example by extraction, derivative formation, dilution, stirring, temperature control, admixing reagents or the like, further for sampling from vials 1, from cells in titration plates or other sample keeping devices, by means of throughflow cuvettes, sample loops, etc., further for sample discharge such as for introducing the respectively taken sample into a sample discharge device of the analytical instrument, further for transferring samples or samplers between various stations and/or for preparing samplers, for example by rinsing. Shown by way of example is the sample handling device for sampling and for introducing the sample taken, for example, above the gas chromatograph, on which there are mounted a large number of vials 1 containing samples in predetermined positions in two groups on corresponding trays. Further stations, for example a rinsing station for samplers, a station for stirring and controlling the temperature of samples, or a station for holding and admixing reagents or the like, can additionally be provided.

The sample handling device comprises a horizontal slide guide 2 for a cross slide 3 which can be moved along the slide guide 2 and which, in addition, can be moved in the plane of the slide guide 2 at right angles to the slide guide 2, so that it is possible to move to all stations. At one end of the cross slide 3 there is a holding arm 4 which can be moved vertically. In this embodiment, a bracket 5 is fixed to the ends of the slide guide 2, on which bracket, on the side facing the slide guide 2, supports 6 for samplers 7 are arranged. However, the supports 6 can also be fixed in another way, for example on the gas chromatograph itself. The holding arm 4 may also be a pivot arm, which is accordingly arranged such that it can move.

For example, for the purpose of sampling with a sample holder (syringe) change, the cross slide 3 moves the holding arm 4 into a position adjacent to a specific support 6, removes the sampler 7 there, moves from there over a vial 1 containing the desired sample, lowers the sampler 7 into the vial in order to take the sample, in order then to move the sampler 7 until it is above a (not illustrated) sample discharge device belonging to the gas chromatograph, to introduce the sampler 7 into the sample discharge device and, depending on the type of sampler 7, either to carry out the sample discharge itself or to place the sampler 7 in the sample discharge device.

Figure 2:
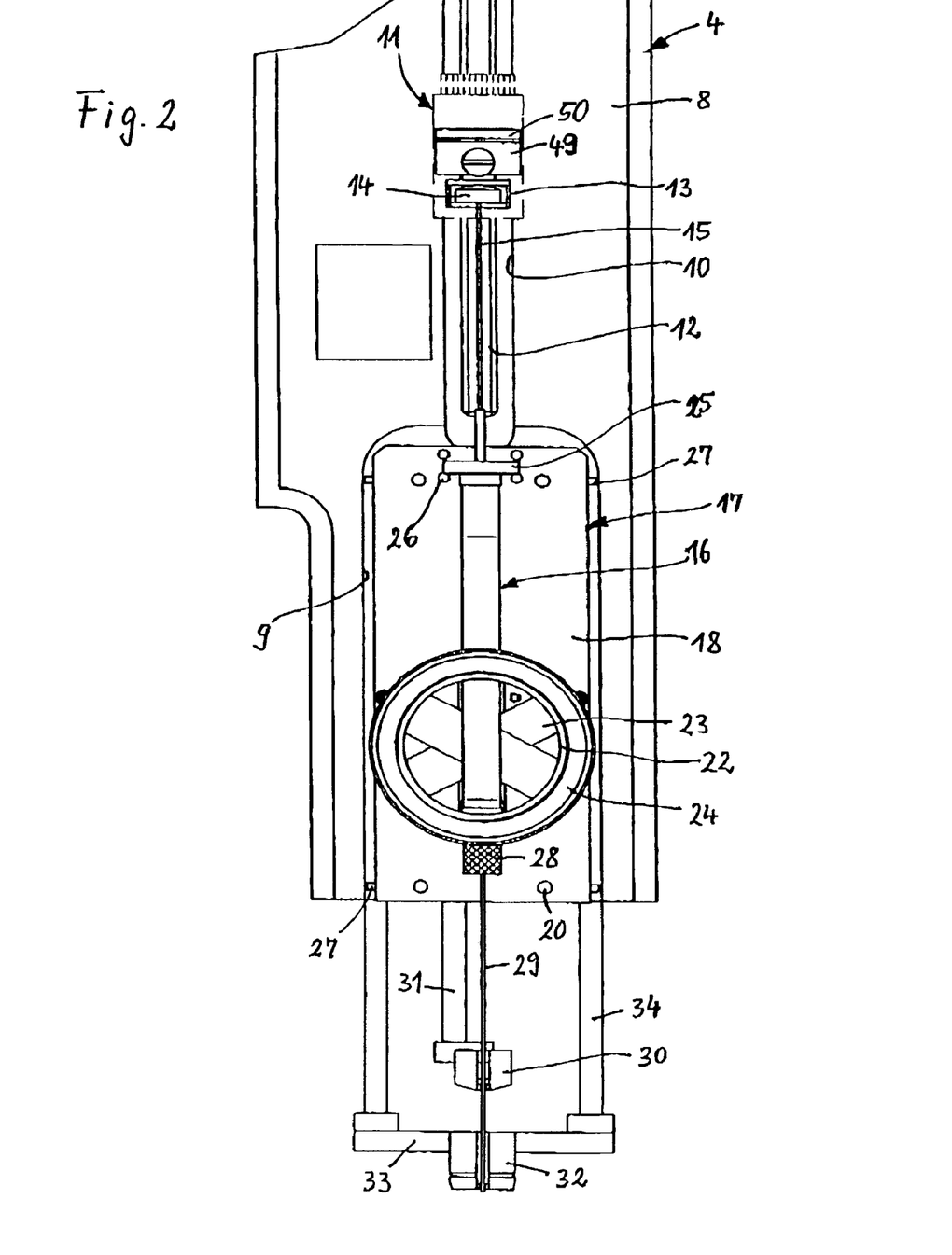
FIG. 2 shows, as a detail, a front view of a holding arm of the sample handling device of FIG. 1.

As can be seen from FIG. 2, the holding arm 4 comprises a plate 8 which, for reasons of space, can be provided with a depression 9 opening at the free end of the arm. Arranged above the depression 9 is a vertical guide groove 10 for an actuator 11, also serving as a piston holder in this exemplary embodiment. The actuator 11 engages in a spindle 12, which can be rotated by a drive, not shown, in order to move the actuator 11 in the longitudinal direction of the holding arm 4, that is to say in the vertical direction. The actuator 11 has a holding piece 13 open at the front for the insertion of an actuating head 14 of a sampler formed in this exemplary embodiment as a syringe 16 above a piston rod 15 of a piston of a sampler.

A holder 17 of the respective sampler, in this exemplary embodiment of the syringe 16, can be placed within the depression 9. The holder 17 comprises a plate 18 which, on the rear, has two sheet metal strips 19 and a plurality of positoning pins 20. Permanent magnets 21 are let into the plate 8 of the holding arm 4 opposite the sheet metal strips 19, so that the holder 17 is held by the permanent magnets 21 and is positioned by the positioning pins 20 above the corresponding holes located in the plate 8.

Figures 7, 8:
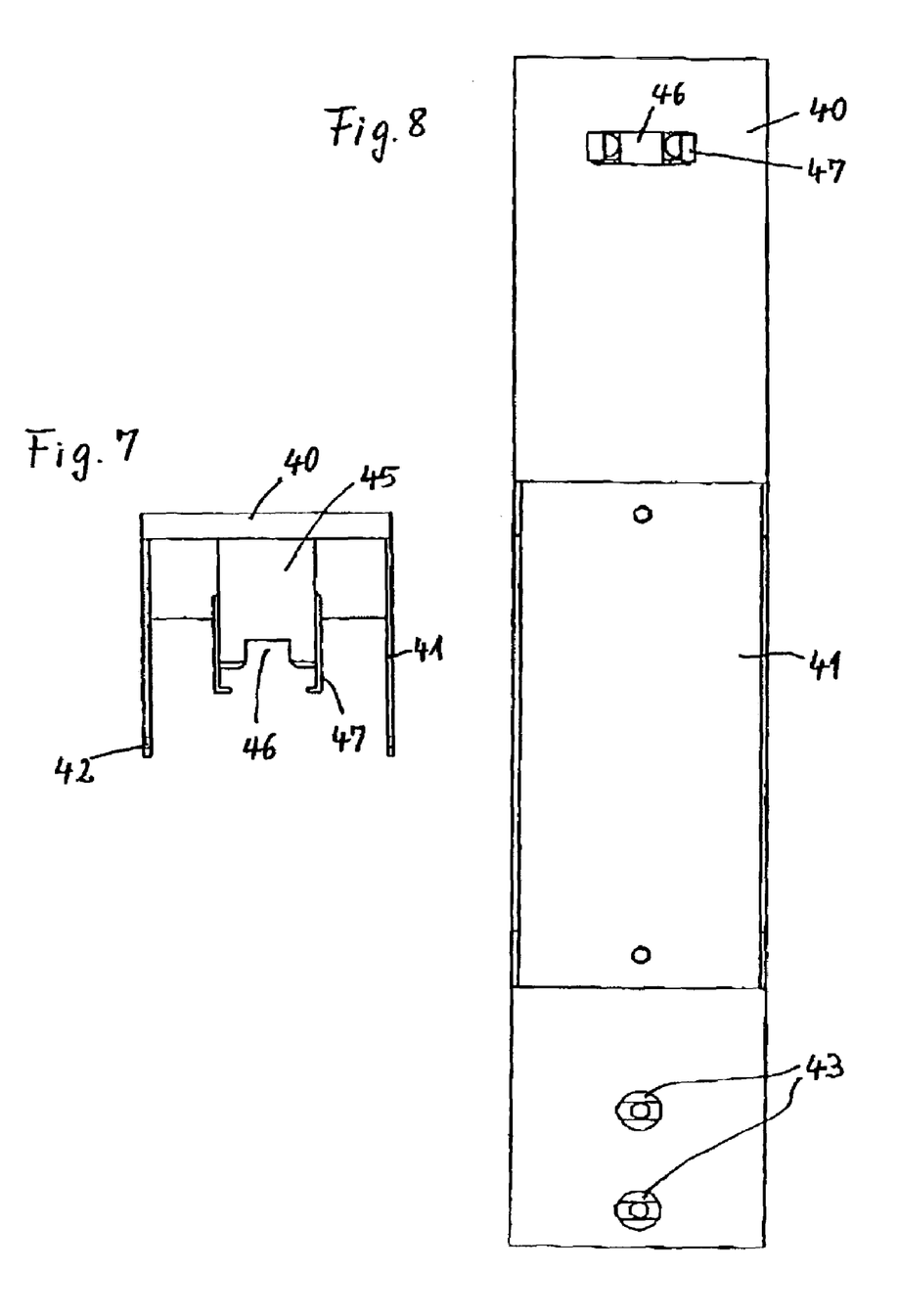
FIGS. 7 and 8 show the holder according to FIGS. 5, 6 additionally in plan view and front view.

In order to be able to accommodate syringes 16 with different diameters, the plate 18 can carry on the front side a ring 22, which has crossing passages 23 for this purpose and can be rotated into corresponding latching positions (for example via a spring-loaded ball which interacts with a matching recess in the plate 18), in which positions the necessary passage is aligned with the longitudinal direction of the holding arm 4. Screwed onto the ring 22 is a ring 24, in order to hold the syringe 16. In addition, on the front side of the plate 18 there is arranged a mount for the syringe flange 25 which, in the exemplary embodiment illustrated, is formed by four pins 26.

In addition, the plate 18 has on each side, at the top and bottom, in each case a pin 27, whose function will be explained later.

Figure 3:
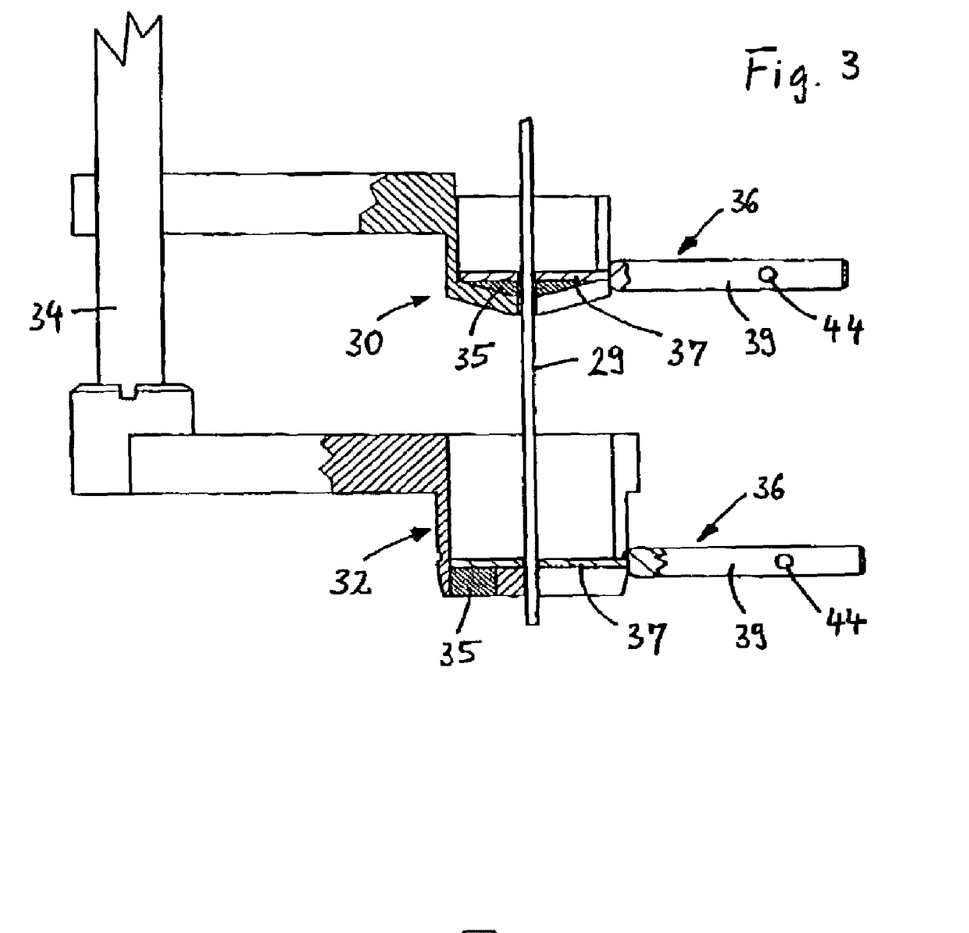
FIG. 3 shows a needle guide holder of the holding arm in section.

The syringe 16 has a needle 29, which can possibly be exchanged via a nut 28. At the lower free end of the holding arm 4, a needle guide holder 30 of smaller diameter is provided at the end of a rod 31 which can be pressed upwards counter to spring prestress and, at a distance below this, a needle guide holder 32 of larger diameter on a yoke 33, which is arranged at the end of two rods 34 that can be pressed upwards against spring prestress. The needle guide holder 32 can accommodate the needle guide holder 30 within itself.

Figure 4:
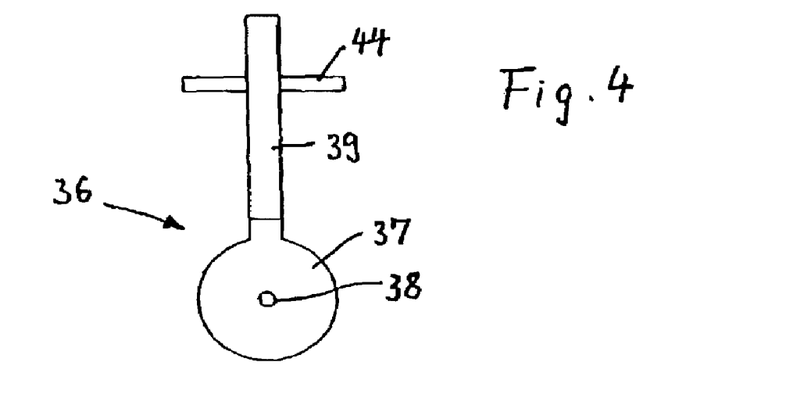
FIG. 4 shows a needle guide in plan view.

The needle guide holders 30, 32 are sleeves which are open at the top and closed at the bottom and slotted from the front side beyond the centre and have permanent magnets 35 inserted at the bottom. The needle guide holders 30, 32 are used to accommodate a needle guide 36 in each case, which comprises a round sheet metal disc 37 with a central opening 38 for the needle 29 with a pin 39 fixed thereto.

Figure 5:
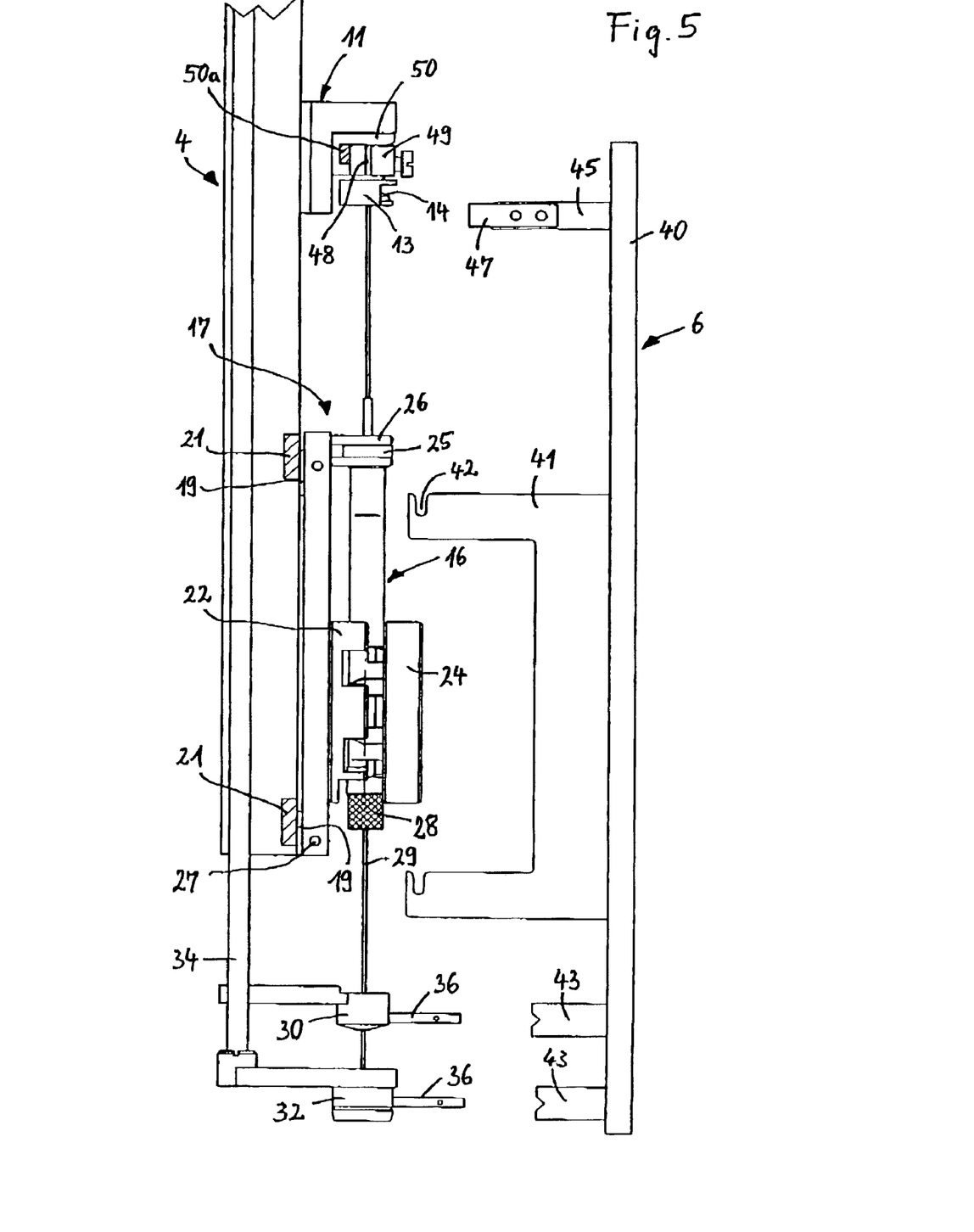
FIGS. 5 and 6 show, in side view and as details, the holding arm and a holder for a holder of a sampler.
Figure 6:
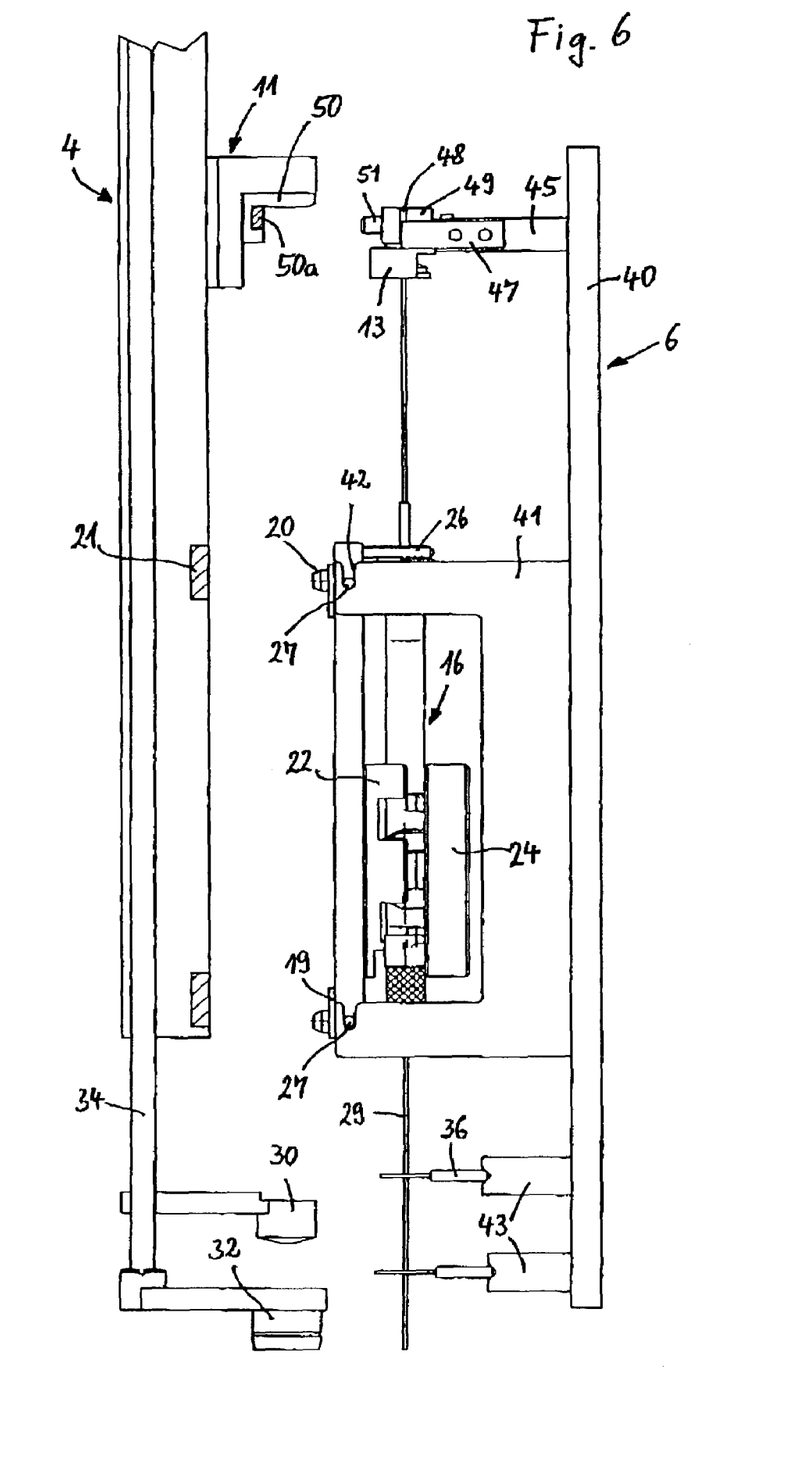

The supports 6 in each case comprise a plate 40, to which in its central region there is fixed a U-shaped bracket 41, whose lateral limbs each have two vertical holding slots 42 for the pins 27 of the holder 17, the spacing of the lateral limbs corresponding substantially to the width of the plate 18.

Also arranged on the plate 40 are two holding bushes 43 for the pins 39 of the needle guides 36, arranged one above the other on the side facing the holding arm 4. The holding bushes 43 are notched horizontally on the entry side, in order to accommodate a transverse pin 44 on the pin 39. The transverse pin 44 extends in the plane of the sheet metal disc 37, so that the latter is aligned horizontally as a result.

Furthermore, at the upper end of plate 40 there is provided a projection 45 which has a depression 46 and to which in each case an angled holding plate 47 is fixed at the side. The angled holding plates 47 serve to be pushed into vertical slots 48 in a removable head 49 of the actuator 11. The piston holder 11 bears an angled piece 50 which closes the vertical slots 48 at the top and opposite which the head 49 can be positioned via a positioning pin 51. In addition, the head 49 is held on the angled piece 50 by one or more permanent magnets 50a.

In order to transfer a syringe 16, the holding arm 4 moves, for example, from the position illustrated in FIG. 5 up to the holder 6, until the vertical slots 48 are located over the angled portions of the holding plates 47. In this position, the pins 27 are also located above the holding slots 42, and the pins 39 of the needle guides 36 are accommodated at the ends by the holding bushes 43. The holding arm 4 is then lowered, so that the plates 47 come into engagement with the vertical slots 48 and the pins 27 with the holding slots 42. This also achieves the situation where the needle guides 36 are separated from the needle guide holders 30, 32, counter to the force of the permanent magnets 35. The holding arm 4 is then moved horizontally away from the support 6. In this case, the support 6 holds the holder 17 back counter to the force of the permanent magnets 21 via the engagement of the pins 27 with the holding slots 42, so that the holding arm 4 is separated from the holder 17.

Transferring a holder 17 from the support 6 is carried out in a correspondingly converse way.

During sampling or during sample discharge, the holding arm 4 with the holder 17 moves into the appropriate position and is lowered until the needle guide holder 32 is located above the appropriate insertion opening for the needle 29. It is then lowered further, while guiding the needle 29, the needle guide holder 30 being accommodated by the needle guide holder 32 and, finally, the entire needle being inserted approximately as far as the nut 28. A sample is then taken by means of an appropriate suction stroke or a sample taken is injected by means of a pressure stroke, in each case effected by the spindle 12. During these actions, in which the piston is moved within the syringe 16, the positioning pins 20 are used to hold the holder 17 and therefore the syringe 16 against vertical displacement.

If use is made of a fibre coated for the adsorption of substances to be examined, then this fibre is arranged in the syringe 16, fixed to its piston, and pushed out appropriately through the needle 29 for the purpose of sampling or sample discharge.

Instead of the permanent magnets 21, a detent which can be released by a pulling force can also be provided for the positioning pins 20 in the plate 8. This also applies to holding the head 49 by means of the actuator 11. In addition, the respective holding can also be carried out electromagnetically or by means of a mechanical interlock.

Instead of or in addition to the positioning pin 51, the actuator 11 can have a horizontal guide groove for a corresponding extension on the angular piece 50.

Figure 9:
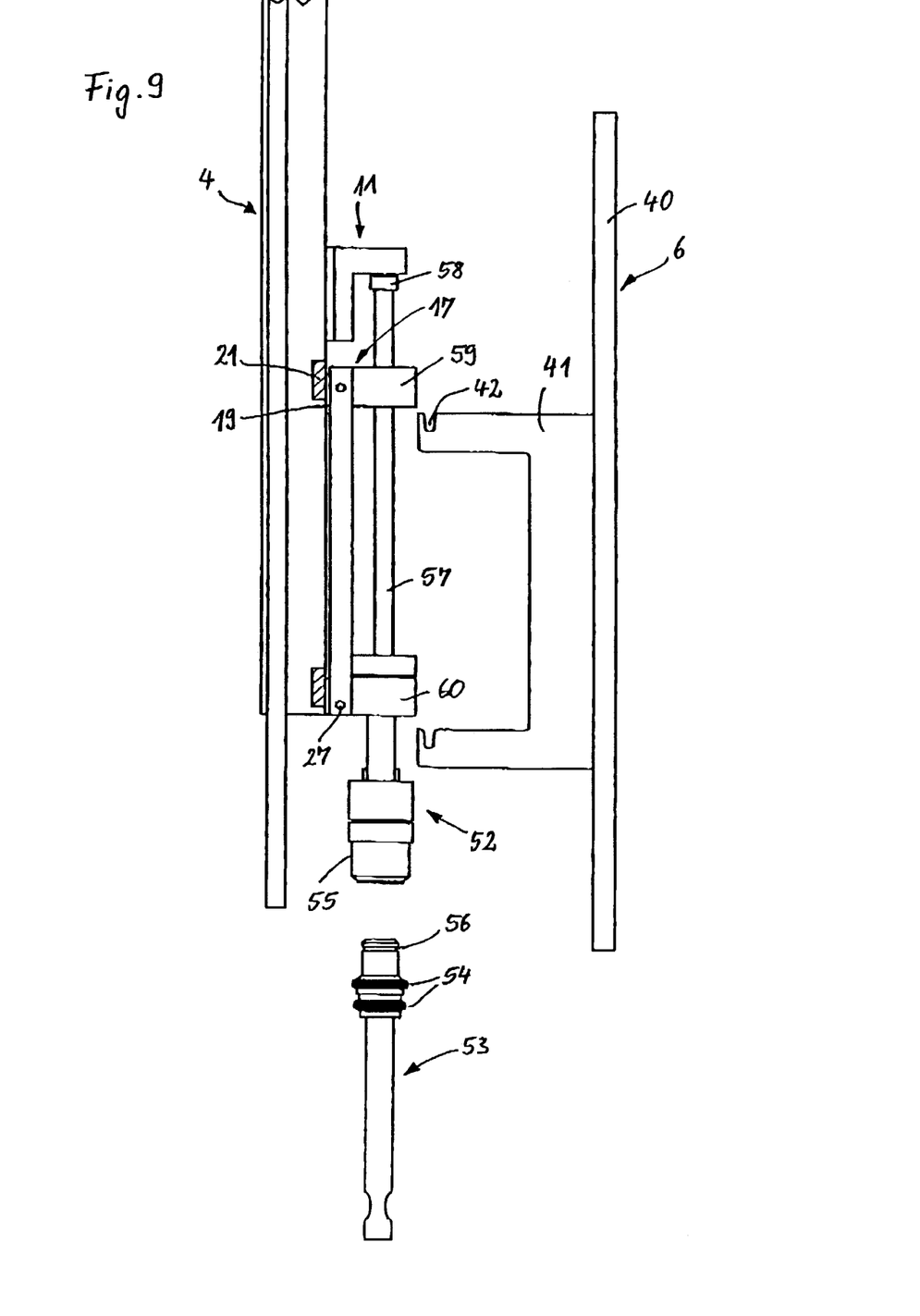
FIG. 9 shows, in side view, one embodiment for handling a sample tube.

In the embodiment illustrated in FIG. 9, the sample handling device is used for handling a sample tube 53 which is located on a gripper 52, which, for example, accommodates a pin with a coating that adsorbs substances to be examined and which can be inserted into a discharge opening in a gas chromatograph sealed off by seals 54, the substances to be examined then being desorbed thermally, for example.

The gripper 52 has a holding head 55 for one end of the sample tube 53, with the holding head 55 having in its interior a plurality of balls arranged equidistantly in the circumferential direction, for example three balls which are spring-loaded inwards and which engage in a groove 56 on the valve head of the sample tube 53, in order to hold the latter. The gripper 52 further has an actuating rod 57 with a piston arranged under spring stress in the holding head 55, and an actuating head 58. The actuating rod 57 can be pressed into the holding head 55 against the spring bias, so that the balls in the interior of the holding head 55 come out of engagement with the groove 56, and the sample tube 53 is released. This can be done in that, if the sample tube 53 is held in a specific position, for example in a sample device of a gas chromatograph or a transfer station or the like, by means of the spindle 12, the actuator 11 acting on the actuating head 58 is moved appropriately. Instead of the balls, expandable claws or springs can also be provided.

The actuating rod 57 is held by a mounting 59 at the upper end of the plate 18 such that it can be displaced longitudinally and therefore pressed into the holding head 55, and the holding head is held by a mounting 60 at the lower end of the plate 18. As in the preceding example, the plate 18 can be suspended in a holder 6 and can be removed from the holding arm 4.

Figure 10:
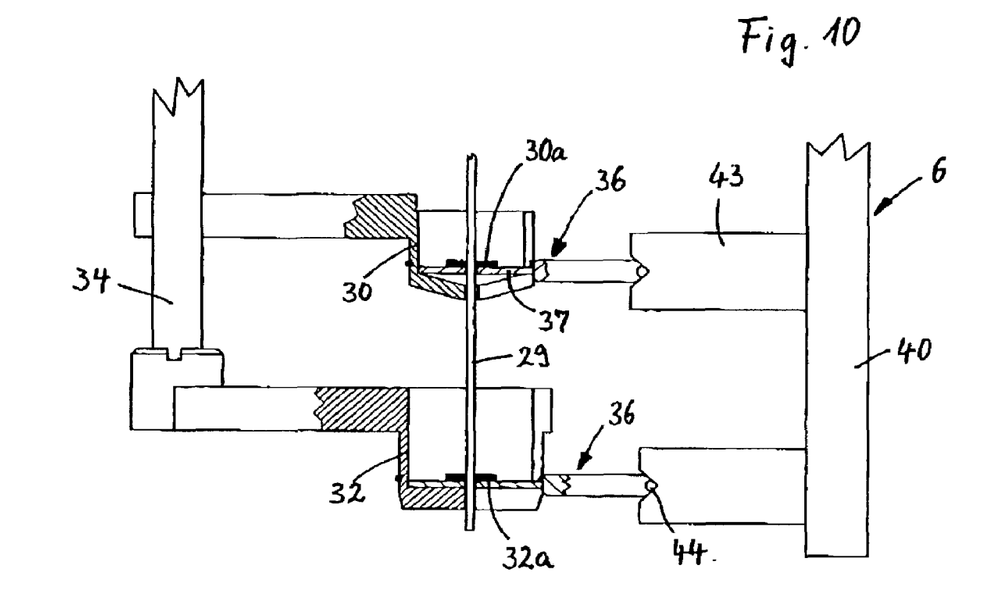
FIG. 10 shows, in section, a further embodiment of a needle guide device.
Figure 11:
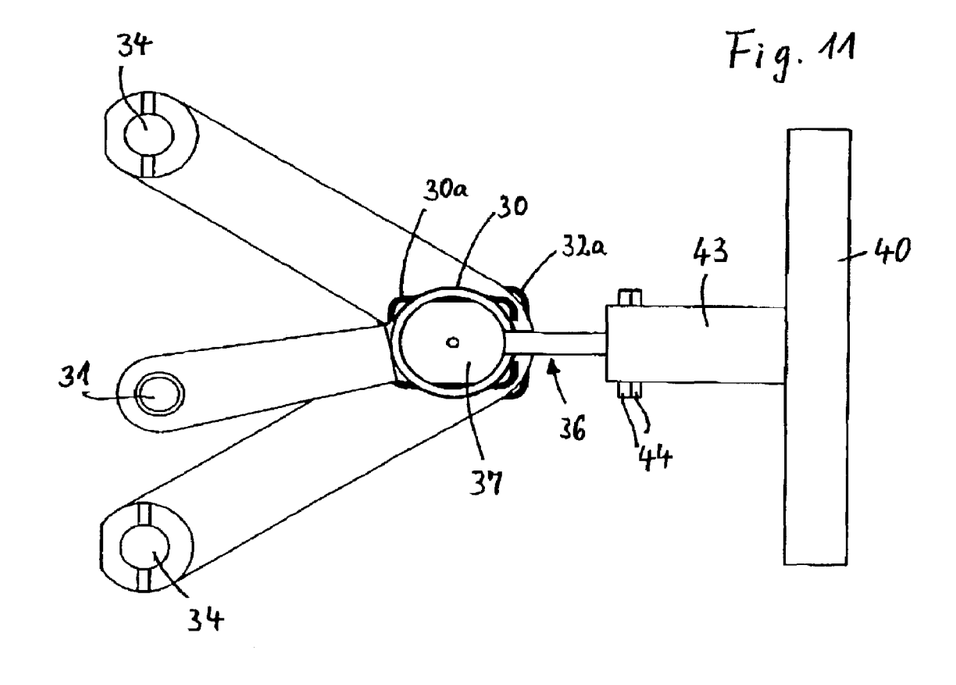
FIG. 11 shows a plan view of the needle guide device from FIG. 10.

In the embodiment illustrated in FIGS. 10, 11, as compared with the embodiment of FIG. 3, the needle guides 37 are not held in the needle guide holders 30, 32 by magnets but by stirrup-shaped wire springs 30a, 32a, whose limbs project on two opposite sides through corresponding slots in the needle guide holders 30, 32 into the interior of the latter above the respective needle guide 37 and, as a result, hold these firmly. When the holding arm 4 is moved downwards, the limbs of the wire springs 30a, 32a are expanded and therefore the needle guides 37 are released.

Figure 12:
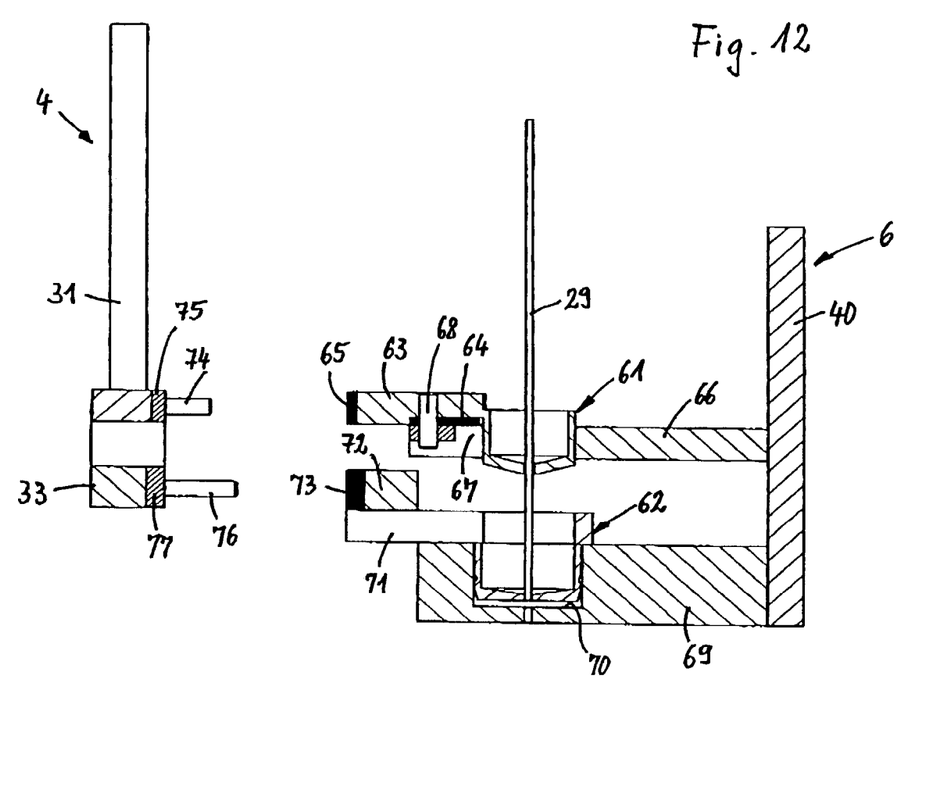
FIG. 12 shows, in section, an additional embodiment of a needle guide device.

In the embodiment illustrated in FIG. 12, needle guides 61 and 62 are formed in a pot shape with a passage opening at the bottom for the needle 29 of the syringe 16, it being possible for the lower needle guide 62 to accommodate the upper needle guide 61. The needle guide 61 is provided with an extension 63 which, on the underside, bears a permanent magnet 64, and on its free end, bears a further permanent magnet 65. The first serves to hold the needle guide 61 on a holding plate 66 which is fixed to the plate 40 and has a corresponding holding recess 67 for the needle guide 61. Centring is carried out via a pin 68, which engages in a slot in the holding plate 66.

Under the holding plate 66 there is a further holding plate 69 with a holding recess 70 for the needle guide 62. The latter has a fork-like extension 71 with a yoke 72, which bears a permanent magnet 73 at the centre.

The rod 31 bears two pins 74 which, for this purpose, extend at right angles in the direction of the needle guide 61 to engage in corresponding holes in the front of the extension 63, and also a mating piece 75 for the permanent magnet 65. The yoke 33 likewise bears two pins 76 which, for this purpose, extend at right angles in the direction of the needle guide 62 to engage in corresponding holes in the front of the yoke 72, and also a mating piece 77 for the permanent magnet 73.

If the pins 74 and 76 are brought into engagement with the extension 63 and the yoke 72, then by moving the holding arm 4 and therefore the rods 31, 34 up, the needle guides 61, 62 with the needle 29 can be taken off the holding plates 66, 69, and therefore the syringe 16 can be accepted from the support 6 by the holding arm 4 or transferred to the holder 6 by moving the holding arm 4 down and away.

The mating pieces 75, can also be interchanged with the permanent magnets 65, 73.

While the invention has been shown and described with reference to the preferred embodiments, it should be apparent to one ordinary skilled in the art that many changes and modifications may be made without departing from the spirit and scope of the invention.

What is claimed is:

1. A sample handling device for an analytical device, comprising a sampler provided with a holder, a transportable holding arm for the holder and a support for the holder, said support being arranged in a stationary manner independent of the holding arm, said holder being transferable between a suspended position on the support and a position located on the holding arm, and being releasable from the holding arm by a pulling force exerted on the holding arm substantially perpendicular to the longitudinal direction of the holding arm.

2. The device according to claim 1, wherein the support has a bracket for suspending the holder.

3. The device according to claim 1 wherein the holder comprises a plate which has lateral pins to hook into the support.

4. The device according to claim 1, wherein the holder is held on the holding arm via magnetic force or releasably mechanically latched or releasably locked.

5. The device according to claim 1, wherein the holder has positioning pins that can be accommodated by corresponding holes in the holding arm.

6. The device according to claim 1, wherein the holding arm bears a displaceable actuator for actuating a gripper or a piston of a sampler held by the holder.

7. The device according to claim 6, wherein the actuator has a head that can be hooked into the support and removed from a piston holder to hold an actuating element of the gripper or of the sampler.

8. The device according to claim 7, wherein the head has opposite lateral slots, while the support has a mounting to engage in the slots.

9. The device according to claim 1, wherein the holder bears a ring which comprises crossing passages for different samplers, is rotatable into corresponding latching positions on the holder and on to which a ring can be screwed in order to clamp the sampler firmly.

10. The device according to claim 1, wherein at least one needle guide for a needle of the sampler is provided, which is transferable between the holding arm and the support having the sampler.

11. The device according to claim 10, wherein the needle guide is a disc provided with a passage opening for the needle and with a pin fixed thereto, the holding arm comprising an associated needle guide holder, into which the disc can be inserted from above, while the support has a bush to accommodate the pin.

12. The device according to claim 11, wherein the disc can be held in the needle guide holder by means of magnetic force.

13. The device according to claim 11, wherein the disc can be held in the needle guide holder by means of spring force.

14. The device according to claim 11, wherein the pin bears a transverse pin which can be accommodated by a notch extending parallel to the plane of the disc in the bush.

15. The device according to claim 11, wherein the needle guide holder can be moved into a second needle guide holder.

16. The device according to claim 10, wherein the needle guide can be coupled to the holding arm via an extension and can be inserted in a holding plate of the support.

17. The device according to claim 16, wherein the needle guide can be coupled to the holding arm via magnetic force and pins.

18. The device according to claim 16, wherein the needle guide can be moved into a second needle guide.

19. The device according to claim 1, wherein the holder has a retaining holder which is open towards the support for a flange of the sampler.

20. The device according to claim 1, wherein the holder has a mounting for an actuating rod of a gripper for a sample tube.

* * * * *